(12) United States Patent
Luo et al.

(10) Patent No.: US 9,171,873 B2
(45) Date of Patent: Oct. 27, 2015

(54) LIGHT SENSING INTEGRATED CIRCUIT AND MANUFACTURING METHOD OF SENSING INTEGRATED CIRCUIT

(71) Applicant: Taiwan Semiconductor Manufacturing CO., LTD., Hsinchu (TW)

(72) Inventors: Tzo-Hung Luo, Taichung (TW); Chin-Hung Chiang, Hsinchu (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 0 days.

(21) Appl. No.: 14/156,860

(22) Filed: Jan. 16, 2014

(65) Prior Publication Data

US 2015/0200215 A1    Jul. 16, 2015

(51) Int. Cl.
| | |
|---|---|
| *H01L 21/768* | (2006.01) |
| *H01L 27/144* | (2006.01) |
| *H01L 31/0232* | (2014.01) |
| *H01L 31/0216* | (2014.01) |
| *H01L 21/77* | (2006.01) |
| *H01L 21/02* | (2006.01) |
| *H01L 31/02* | (2006.01) |

(52) U.S. Cl.
CPC ...... *H01L 27/1443* (2013.01); *H01L 21/02057* (2013.01); *H01L 21/02568* (2013.01); *H01L 21/768* (2013.01); *H01L 21/77* (2013.01); *H01L 31/02005* (2013.01); *H01L 31/02161* (2013.01); *H01L 31/02327* (2013.01)

(58) Field of Classification Search
CPC .......................................... H01L 31/06
USPC .......... 250/214.1, 208.1, 338.4, 332, 339.02; 257/759
See application file for complete search history.

(56) References Cited

U.S. PATENT DOCUMENTS

| | | | | |
|---|---|---|---|---|
| 5,900,630 | A * | 5/1999 | Tang et al. | 250/338.4 |
| 6,288,388 | B1 * | 9/2001 | Zhang et al. | 250/214.1 |
| 2008/0283954 | A1 * | 11/2008 | Shim | 257/443 |
| 2009/0014056 | A1 * | 1/2009 | Hockaday | 136/247 |
| 2009/0127435 | A1 * | 5/2009 | Mochizuki et al. | 250/208.1 |

* cited by examiner

*Primary Examiner* — Sheng Zhu

(57) ABSTRACT

A manufacturing method of a sensing integrated circuit including the following acts. A plurality of transistors are formed. At least one dielectric layer is formed on or above the transistors. A plurality of connecting structures are formed in the dielectric layer. The connecting structures are respectively and electrically connected to the transistors. A plurality of separated conductive wells are respectively formed in electrical contact with the connecting structures.

20 Claims, 4 Drawing Sheets

LIGHT SENSING INTEGRATED CIRCUIT AND MANUFACTURING METHOD OF SENSING INTEGRATED CIRCUIT

BACKGROUND

A sensor is a converter used to measure a physical quantity and then convert it into a signal. This signal may be read by an observer or by an electronic instrument. For example, a photodiode may convert the measured light input into a proportional current output, and a deoxyribonucleic acid (DNA) sensor may convert the measured energy of hydrogen bonds into an output voltage. The sensitivity of the sensor represents how much of the output when measuring the physical quantity, and a sensor with higher sensitivity can sense more tiny amount of the physical quantity.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
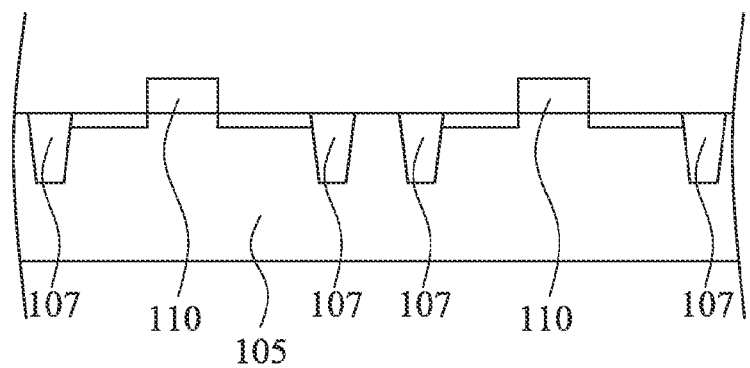
FIG. 1 to FIG. 7 are cross-sectional views of a method for manufacturing a sensing integrated circuit according to various embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

As used herein, the terms "comprising," "including," "having," "containing," "involving," and the like are to be understood to be open-ended, i.e., to mean including but not limited to.

In the digital world, integrated circuit (IC) technology continues to shrink in size. The pure digital technologies focus on the digital density and low cost. However, for a sensor with higher digital density and low cost, the sensitivity may be reduced, or crosstalk between adjacent two sensing units of the sensor may occur. Therefore, a light sensing integrated circuit and a method of a sensing integrated circuit can be provided.

FIG. 1 to FIG. 7 are cross-sectional views of a method for manufacturing a sensing integrated circuit according to various embodiments of the present disclosure. Reference is made to FIG. 1. A manufacturer may form a plurality of transistors 110. In greater detail, the manufacturer may form the transistors 110 on a substrate 105. To separate the transistors 110 from each other, a plurality of insulating portions 107 may be embedded in the substrate 105 and disposed between adjacent two of the transistors 110. In some embodiments, the substrate 105 may be made of silicon, gallium nitride, or any combination thereof. The insulating portions 107 may be shallow trench isolations (STIs) and may be made of silicon oxide. At least one of the transistors 110 may be made of doped semiconductors.

Figure 2:
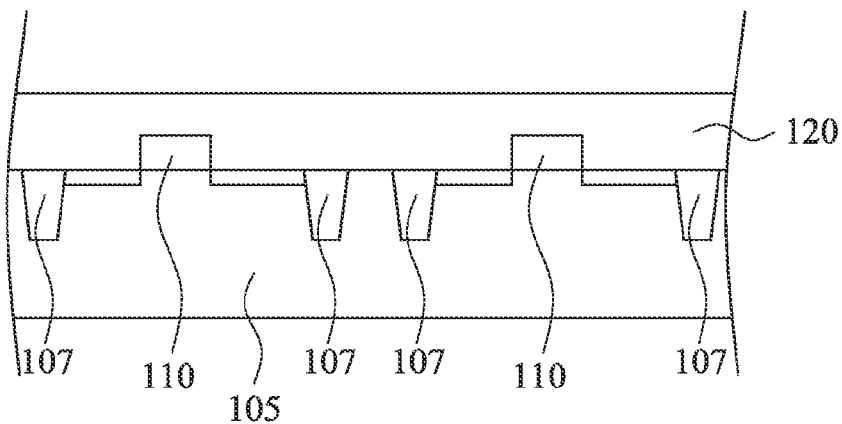

Reference is made to FIG. 2. Subsequently, the manufacturer may form at least one dielectric layer 120 on or above the transistors 110. Taking FIG. 2 as an example, the dielectric layer 120 is formed on the transistors 110. In some embodiments, the dielectric layer 120 may be made of silicon nitride (SiNx), silicon oxide (SiOx), silicon nitride oxide (SiOxNy), or any combination thereof.

Figure 3:
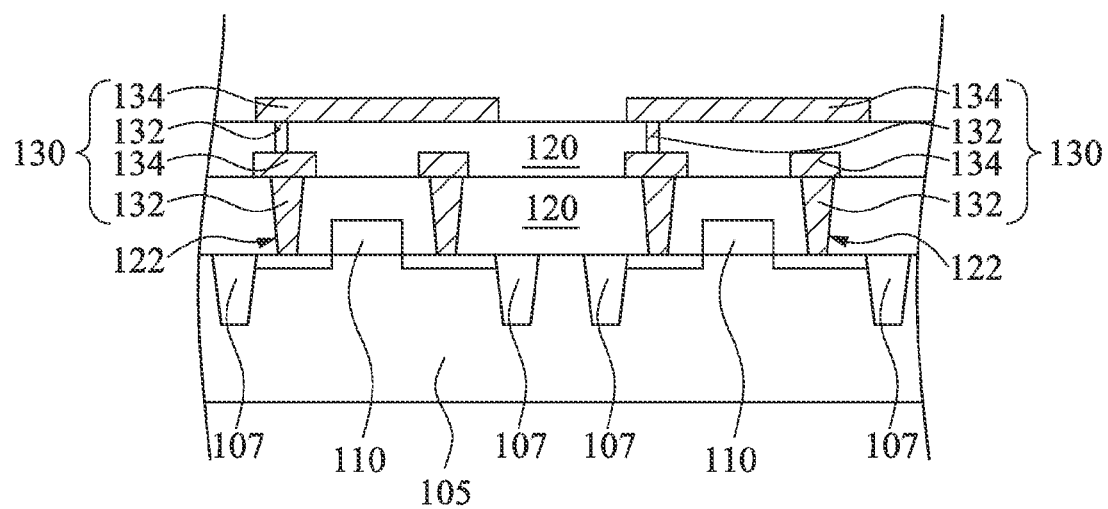

Reference is made to FIG. 3. The manufacturer may form a plurality of connecting structures 130 in the dielectric layer 120. The connecting structures 130 are respectively and electrically connected to the transistors 110. For example, the manufacturer may form at least one via hole 122 in the dielectric layer 120 so that at least a portion of the transistor 110 may be exposed by the via hole 122. Taking FIG. 3 as an example, there are four via holes 122 in the dielectric layer 120 to expose four portions of the transistors 110, respectively. The connecting structures 130, which may include a plurality of plugs 132, are formed in the via holes 122, such that the connecting structures 130 may be electrically connected to the transistors 110, respectively. In some embodiments, the connecting structures 130 may be made of metal, such as titanium (Ti), aluminum (Al), copper (Cu), silver (Ag), or any combination thereof.

In some embodiments, the number of the dielectric layer 120 may be plural so that the dielectric layers 120 may be stacked to each other, and the connecting structures 130 may further include a plurality of wires 134. A portion of the wires 134 may be formed between adjacent two of the dielectric layers 120, and another portion of the wires 134 may be exposed by the dielectric layers 120. The two portions of the wires 134 are separated by one of the dielectric layers 120 and are electrically connected to each other through the plugs 132 of the connecting structure 130. It should be noted that although there are two dielectric layers 120 in FIG. 3, the claimed scope should not limit to this respect. A person having ordinary skill in the art may design a proper number for the dielectric layer 120 according to actual requirements. In some embodiments, if the wires 134 of the connecting structure 130 are not formed, there may be one dielectric layer 120 formed on or above the transistors 110.

Figure 4:
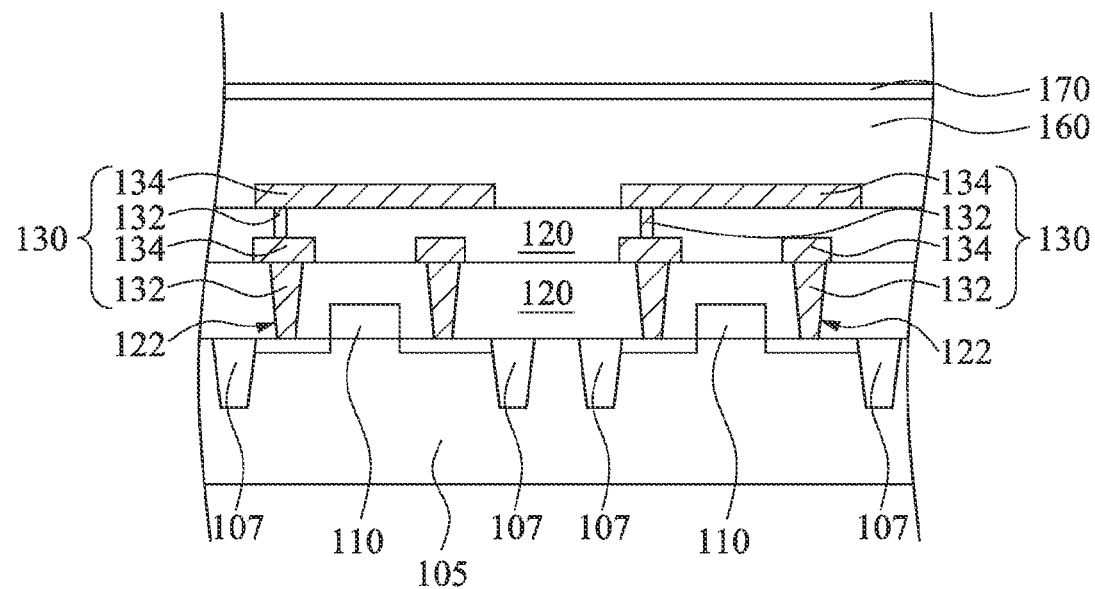

Reference is made to FIG. 4. Subsequently, the manufacturer may form a plurality of separated conductive wells respectively in electrical contact with the connecting structures 130. In greater detail, the manufacturer may form a passivation layer 160 on the connecting structure 130. For example, the manufacturer may form the passivation layer 160 on the wires 134. In some embodiments, the passivation layer 160 may be made of silicon nitride ($SiN_x$), silicon oxide ($SiO_2$), silicon oxynitride ($SiO_xN_y$), or any combination thereof. In some embodiments, the manufacturer may form at least one anti-reflective coating (ARC) layer 170 on or above the passivation layer 160. The anti-reflective coating layer 170 may be made of silicon nitride ($SiN_x$), silicon oxynitride ($SiON_x$), or combinations thereof.

Figure 5:
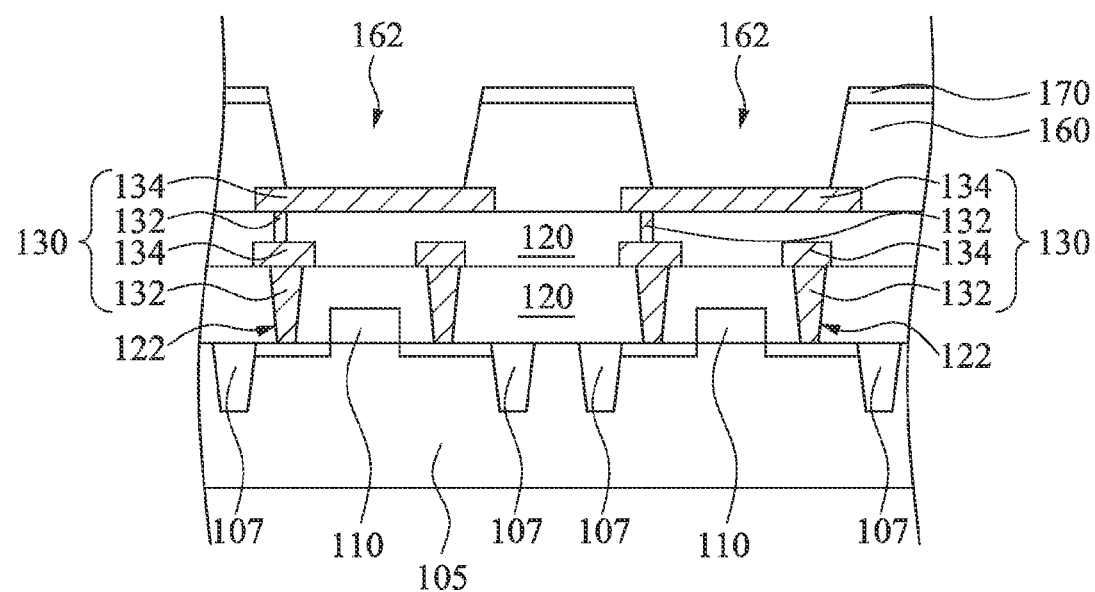

Reference is made to FIG. 5. The manufacturer may form a plurality of through holes 162 in the passivation layer 160. For example, in some embodiments, the manufacturer may form a mask layer on the anti-reflective coating layer 170 and then pattern the mask layer. Then, the manufacturer may sequentially pattern the anti-reflective coating layer 170 and the passivation layer 160 through the patterned mask layer to form the through holes 162 in the passivation layer 160. In some embodiments, the through holes 162 may respectively expose the wires 134. However, if the wires 134 are not formed on the dielectric layers 120, i.e. the passivation layer 160 is formed on the plugs 132 of the connecting structure 130, the through holes 162 of the passivation layer 160 may expose the plugs 132 instead.

Figure 6:
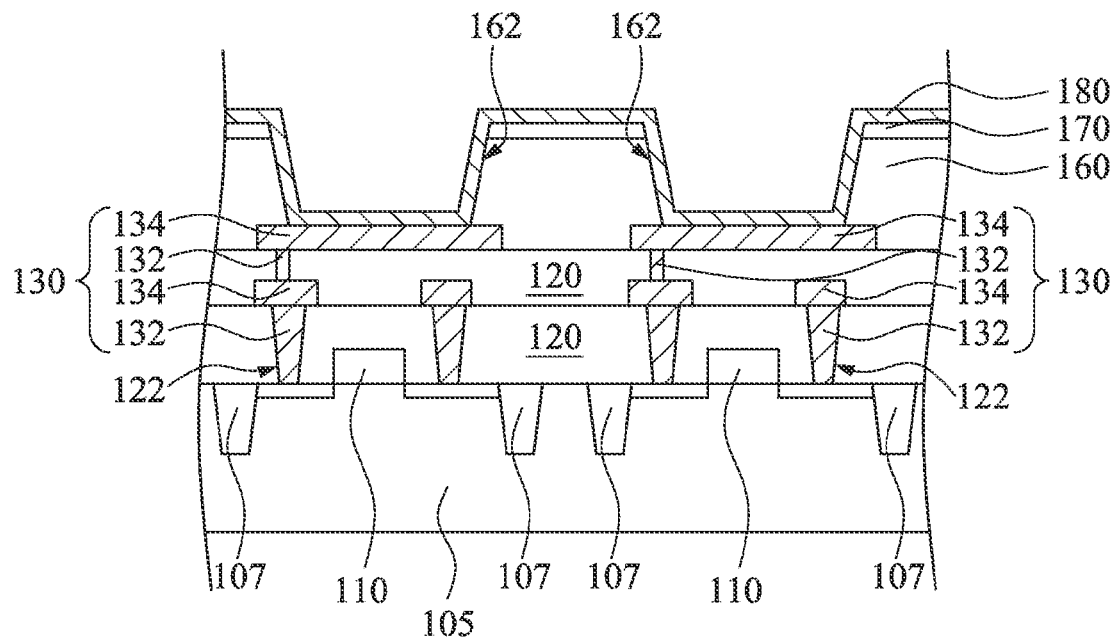

Reference is made to FIG. 6. The manufacturer may conformally form a conductive layer 180 at least covering the passivation layer 160. In some embodiments, the conductive layer 180 covers the anti-reflective coating layer 170, the passivation layer 160, and the wires 134 exposed by the through holes 162. As such, the conductive layer 180 may be electrically connected to the connecting structure 130. In some embodiments, the conductive layer 180 may be made of high conductivity materials, such as titanium (Ti), titanium nitride (TiN), titanium tungsten (TiW), tantalum (Ta), tantalum tungsten (TaN), or any combination thereof.

Figure 7:
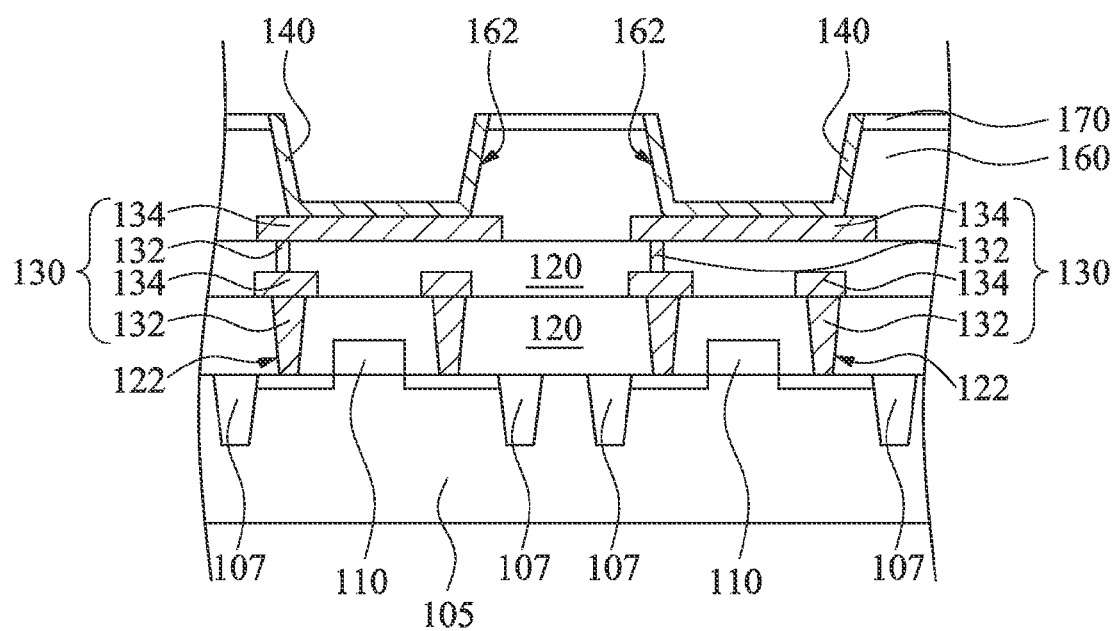

Reference is made of FIG. 7. Subsequently, the manufacturer may remove at least a portion of the conductive layer 180 (see FIG. 6) outside the through holes 162 to form the conductive wells 140 in the through holes 162 of the passivation layer 160. For example, the manufacturer may remove the portion of the conductive layer 180 outside the through holes 162 by chemical mechanical planarization (CMP). In addition, if the anti-reflective coating layer 170 is formed on the passivation layer 160, the anti-reflective coating layer 170 may be a CMP stop layer which is used to control the polishing depth during the CMP process. In some embodiments, since the portion of the conductive layer 180 outside the through holes 162 may be removed by the CMP technique, an additional lithography and etching process may be unnecessary. After the process of FIG. 7, the manufacturing of the sensing integrated circuit is completed.

Structurally, the sensing integrated circuit of FIG. 7 includes a plurality of the transistors 110, at least one of the dielectric layer 120, a plurality of the connecting structures 130, and a plurality of the separated conductive wells 140. The dielectric layer 120 is disposed on or above the transistors 110. The connecting structures 130 are disposed in the dielectric layer 120. The connecting structures 130 are respectively and electrically connected to the transistors 110. The conductive wells 140 are respectively in electrical contact with the connecting structures 130. In some embodiments, the conductive wells 140 of the sensing integrated circuit may be arranged as a two-dimensional array. However, the claimed scope of the disclosure should not be limited in this respect.

In operation, the sensing integrated circuit of FIG. 7 may be disposed in a liquid solution with deoxyribonucleic acid (DNA) molecules. Some of the DNA molecules may move into the conductive wells 140 of the sensing integrated circuit so that the hydrogen ions of the DNA molecules may affect the electrical characteristic of the transistors 110 through the conductive wells 140. Therefore, the information of the DNA molecules may be sensed. In addition, since the conductive wells 140 are separated from each other, crosstalk between adjacent two of the conductive wells 140 may be avoided. Furthermore, in some embodiments, the information of the DNA molecules in the conductive wells 140 may be further transmitted to other devices through the wires 134 of the connecting structures 130. However, the claimed scope of the disclosure should not be limited in this respect.

Figure 8:
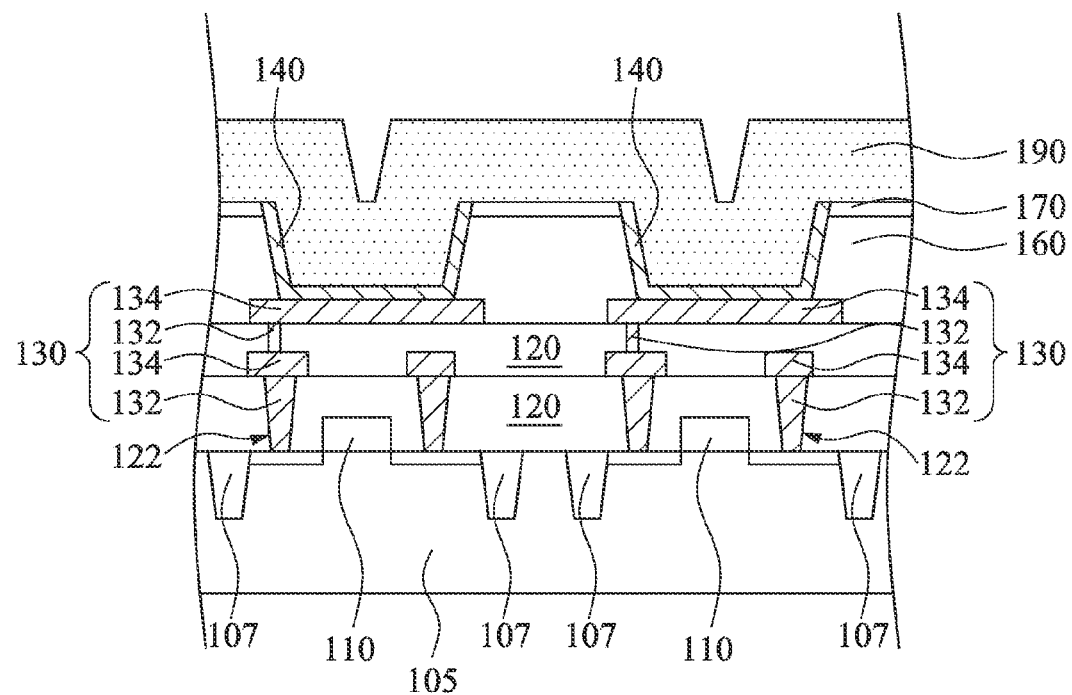
FIG. 8 to FIG. 9 are cross-sectional views of a method for manufacturing a sensing integrated circuit according to various embodiments of the present disclosure.

In some embodiments, the manufacturer may further form a plurality of light sensing films respectively in the conductive wells 140 to form a light sensing integrated circuit. Reference is made to FIG. 8. In greater detail, the manufacturer may firstly form a light sensing layer 190 covering the conductive wells 140. In some embodiments, the light sensing layer 190 may be made of photoconductive materials, such as lead sulfide (PbS), polyvinlcarbazole, selenium (Se), or any combination thereof. The photoconductive materials may become more electrically conductive due to the absorption of electromagnetic radiation such as visible light, ultraviolet light, infrared light, or gamma radiation. For example, PbS is more sensitive to infrared light range.

Figure 9:
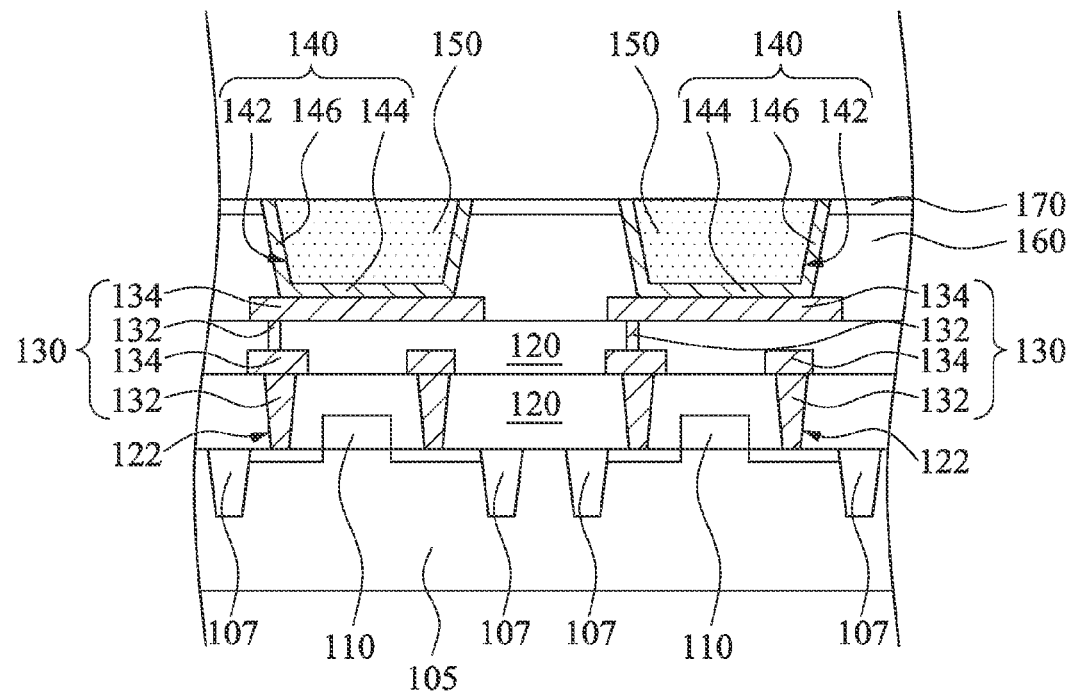

Reference is made to FIG. 9. Subsequently, the manufacturer may remove at least a portion of the light sensing layer 190 (see FIG. 8) outside the conductive wells 140 to form the light sensing films 150 in the conductive wells 140. Therefore, the light sensing films 150 may be separated from each other. In some embodiments, the portion of the light sensing layer 190 may be removed by chemical mechanical planarization (CMP) or photolithography and etching processes. It may be noted that if the portion of the light sensing layer 190 is removed using the CMP technique, other mask layers which may be disposed on the light sensing layer 190 for lithography and etching process may be omitted. After the process of FIG. 9, the manufacturing of the light sensing integrated circuit is completed.

Structurally, the light sensing integrated circuit of FIG. 9 includes a plurality of the transistors 110, at least one of the dielectric layer 120, a plurality of the connecting structures 130, a plurality of the conductive wells 140, and a plurality of the light sensing films 150. The dielectric layer 120 is disposed on or above the transistors 110. The connecting structures 130 are respectively and electrically connecting the conductive wells 140 to the transistors 110. The conductive wells 140 are disposed on or above the dielectric layer 120. The light sensing films 150 are respectively disposed in the conductive wells 140 and thus separated from each other. In some embodiments, the conductive wells 140 of the sensing integrated circuit may be arranged as a two-dimensional array. However, the scope of the claimed disclosure should not be limited in this respect.

In some embodiments, at least one of the light sensing films 150 is made of photoconductive materials such as PbS, polyvinylcarbazole, Se, or any combination thereof. When light is absorbed by the photoconductive materials, the number of free electrons and electron holes increases and raises its electrical conductivity. The transistors 110 may sense the electrical conductivity of the light sensing films 150 through the conductive wells 140 and the connecting structures 130. As such, the light absorbed by the light sensing films 150 may be sensed.

In some embodiments, at least one of the conductive wells 140 is made of high conductivity materials such as Ti, TiN, TiW, Ta, TaN, or any combination thereof. In greater detail, the high conductivity of the conductive wells 140 provides higher sensibility and higher transmission speed of light sensing integrated circuit. As such, the sensibility and the transmission speed may be both improved although the size of the light sensing integrated circuit is shrunk.

In some embodiments, at least one of the conductive wells 140 defines a containing space 142 therein. At least one of the light sensing films 150 is disposed in the containing space 142, and the containing space 142 gets narrower towards the dielectric layer 120. In other words, the containing space 142 gets wider away from the dielectric layer 120. With this configuration, the light absorption areas of the light sensing films 150 may be increased while adjacent two of the conductive wells 140 remain separated from each other.

In some embodiments, the conductive well 140 includes a bottom portion 144 and at least one side wall 146 surrounding the containing space 142. The bottom portion 144 may be disposed on the connecting structure 130 so that the bottom portion 144 is electrically connected to the connecting structure 130. The side wall 146 is connected to the edge of the bottom portion 144. Since the light sensing films 150 are disposed in the containing spaces 142, respectively, the electrons and the holes produced from the light sensing films 150 may move to the bottom portion 144 and the side wall 146 and be sensed. In other words, due to a large contact area between the light sensing film 150 and the conductive well 140, the sensitivity of the light sensing integrated circuit of the present disclosure may be enhanced.

In some embodiments, the light sensing integrated circuit may further include at least one passivation layer 160 disposed between adjacent two of the conductive wells 140. In some embodiments, the light sensing integrated circuit may further include at least one anti-reflective coating layer 170 disposed on or above the passivation layer 160. For example, in FIG. 9, the anti-reflective coating layer 170 is disposed on the passivation layer 160. The anti-reflective coating layer 170 may be a CMP stop layer if the conductive wells 140 and/or the light sensing films 150 are performed using CMP technique. In addition, the anti-reflective coating layer 170 may prevent light reflections during the lithography process, such that the light may be avoid to be incident the area which is not desired to be exposed.

It is understood that the embodiments of the light sensing integrated circuit mentioned above is provided as examples and are not intended to be limiting. The light sensing integrated circuit may have different configurations consistent with the spirit of the present disclosure in alternative embodiments depending on design requirements and manufacturing concerns.

According to the embodiments mentioned above, one form of the present disclosure provides the manufacturing method of a sensing integrated circuit including the following acts. A plurality of transistors are formed. At least one dielectric layer is formed on or above the transistors. A plurality of connecting structures are formed in the dielectric layer. The connecting structures are respectively and electrically connected to the transistors. A plurality of separated conductive wells are respectively formed in electrical contact with the connecting structures.

In some embodiments, the method further includes act of forming a plurality of light sensing films respectively in the conductive wells.

In some embodiments, at least one of the light sensing films is made of PbS, polyvinylcarbazole, Se, or any combination thereof.

In some embodiments, the act of forming the light sensing films includes the following acts. A light sensing layer covering the conductive wells is formed. At least a portion of the light sensing layer outside the conductive wells is removed to form the light sensing films in the conductive wells.

In some embodiments, the act of forming the conductive wells includes the following acts. A passivation layer is formed on the connecting structures. A plurality of through holes are formed in the passivation layer. A conductive layer is conformally formed to at least cover the passivation layer. At least a portion of the conductive layer outside the through holes is removed to form the conductive wells in the through holes of the passivation layer.

In some embodiments, removing the portion of the conductive layer outside the through holes are performed by chemical mechanical planarization.

In some embodiments, at least one of the conductive wells is made of Ti, TiN, TiW, Ta, TaN, or any combination thereof.

The acts are not recited in the sequence in which the acts are performed. That is, unless the sequence of the acts is expressly indicated, the sequence of the acts is interchangeable, and all or part of the acts may be simultaneously, partially simultaneously, or sequentially performed.

Another form of the present disclosure provides the light sensing integrated circuit including a plurality of the transistors, at least one of the dielectric layer, a plurality of the connecting structures, a plurality of the conductive wells, and a plurality of the light sensing films. The dielectric layer is disposed on or above the transistors. The connecting structures are respectively and electrically connecting the conductive wells to the transistors. The conductive wells are disposed on or above the dielectric layer. The light sensing films are respectively disposed in the conductive wells and thus separated from each other.

In some embodiments, at least one of the conductive wells defines a containing space therein. At least one of the light sensing films is disposed in the containing space, and the containing space gets narrower towards the dielectric layer.

In some embodiments, at least one of the conductive wells defines a containing space therein. At least one of the light sensing films is disposed in the containing space, and the containing space gets wider away from the dielectric layer.

In some embodiments, the light sensing integrated circuit further includes at least one passivation layer disposed between adjacent two of the conductive wells.

In some embodiments, the light sensing integrated circuit further includes at least one anti-reflective coating layer disposed on or above the passivation layer.

Yet another form of the present disclosure provides light sensing integrated circuit including a plurality of the transistors, at least one of the dielectric layer, a plurality of the connecting structures, a plurality of the conductive wells, and a plurality of the photoconductive materials. The dielectric layer is disposed on or above the transistors. The connecting structures are respectively and electrically connecting the conductive wells to the transistors. The conductive wells are disposed on or above the dielectric layer. The photoconductive materials are respectively disposed in the conductive wells and thus separated from each other.

In some embodiments, at least one of the photoconductive materials is PbS, polyvinlcarbazole, Se, or any combination thereof.

In some embodiments, at least one of the conductive wells defines a containing space therein, at least one of the photoconductive materials is disposed in the containing space, and the containing space gets narrower towards the dielectric layer.

In some embodiments, at least one of the conductive wells defines a containing space therein, at least one of the photoconductive materials is disposed in the containing space, and the containing space gets wider away from the dielectric layer.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A light sensing integrated circuit, comprising:
   a plurality of transistors;
   at least one dielectric layer disposed on or above the transistors;
   a plurality of conductive wells disposed on or above the dielectric layer, wherein the conductive wells respectively define containing spaces therein;
   a plurality of light sensing films respectively and fully disposed in the containing spaces of the conductive wells and thus separated from each other; and
   a plurality of connecting structures respectively and electrically connecting the conductive wells to the transistors.

2. The light sensing integrated circuit of claim 1, wherein at least one of the light sensing films is made of lead sulfide (PbS), polyvinlcarbazole, selenium (Se), or any combination thereof.

3. The light sensing integrated circuit of claim 1, wherein at least one of the conductive wells is made of titanium (Ti), titanium nitride (TiN), titanium tungsten (TiW), tantalum (Ta), tantalum tungsten (TaN), or any combination thereof.

4. The light sensing integrated circuit of claim 1, wherein at least one of the containing spaces gets narrower towards the dielectric layer.

5. The light sensing integrated circuit of claim 1, wherein at least one of the containing spaces gets wider away from the dielectric layer.

6. The light sensing integrated circuit of claim 1, further comprising:
   at least one passivation layer disposed between adjacent two of the conductive wells.

7. The light sensing integrated circuit of claim 6, further comprising:
   at least one anti-reflective coating layer disposed on or above the passivation layer.

8. The light sensing integrated circuit of claim 7, wherein the anti-reflective coating layer is disposed between adjacent two of the conductive wells.

9. The light sensing integrated circuit of claim 1, wherein at least one of the connecting structures comprises:
   a plug connected to the transistor.

10. The light sensing integrated circuit of claim 9, wherein at least one of the connecting structures further comprises:
    a wire disposed on the plug, wherein the plug is connected to the wire and the transistor.

11. The light sensing integrated circuit of claim 1, wherein at least one of the conductive wells comprises:
    a bottom portion disposed on and electrically connected to the connecting structures; and
    at least one side wall connected to an edge of the bottom portion.

12. A light sensing integrated circuit, comprising:
    a plurality of transistors;
    at least one dielectric layer disposed on or above the transistors;
    a plurality of conductive wells disposed on or above the dielectric layer and separated from each other, wherein the conductive wells respectively define containing spaces therein;
    a plurality of photoconductive materials respectively and fully disposed in the containing spaces of the conductive wells and thus separated from each other; and
    a plurality of connecting structures respectively and electrically connecting the conductive wells to the transistors.

13. The light sensing integrated circuit of claim 12, wherein at least one of the photoconductive materials is lead sulfide (PbS), polyvinlcarbazole, selenium (Se), or any combination thereof.

14. The light sensing integrated circuit of claim 12, wherein at least one of the containing spaces gets narrower towards the dielectric layer.

15. The light sensing integrated circuit of claim 12, wherein at least one of the containing spaces gets wider away from the dielectric layer.

16. The light sensing integrated circuit of claim 12, further comprising:
    at least one passivation layer disposed between adjacent two of the conductive wells.

17. The light sensing integrated circuit of claim 16, further comprising:
    at least one anti-reflective coating layer disposed on or above the passivation layer.

18. The light sensing integrated circuit of claim 12, wherein at least one of the connecting structures comprises:
    a plug connected to the transistor.

19. The light sensing integrated circuit of claim 18, wherein at least one of the connecting structures further comprises:
    a wire disposed on the plug, wherein the plug is connected to the wire and the transistor.

20. The light sensing integrated circuit of claim 12, wherein at least one of the conductive wells comprises:
    a bottom portion disposed on and electrically connected to the connecting structures; and
    at least one side wall connected to an edge of the bottom portion.

* * * * *